(12) United States Patent
Katkov et al.

(10) Patent No.: US 9,638,452 B2
(45) Date of Patent: May 2, 2017

(54) METHOD AND SCALABLE DEVICES FOR HYPER-FAST COOLING AND WARMING

(71) Applicants: Igor Katkov, San Diego, CA (US); Vladimir Fedorovich Bolyukh, Kharkov (UA)

(72) Inventors: Igor Katkov, San Diego, CA (US); Vladimir Fedorovich Bolyukh, Kharkov (UA)

(73) Assignee: Celltronix, San Diego, CA (US)

( * ) Notice: Subject to any disclaimer, the term of this patent is extended or adjusted under 35 U.S.C. 154(b) by 710 days.

(21) Appl. No.: 14/011,799

(22) Filed: Aug. 28, 2013

(65) Prior Publication Data

US 2014/0069119 A1 Mar. 13, 2014

Related U.S. Application Data

(60) Provisional application No. 61/741,778, filed on Sep. 12, 2012.

(51) Int. Cl.
*A01N 1/02* (2006.01)
*F25D 3/10* (2006.01)
(Continued)

(52) U.S. Cl.
CPC .............. *F25D 3/10* (2013.01); *A01N 1/0236* (2013.01); *A01N 1/0252* (2013.01);
(Continued)

(58) Field of Classification Search
CPC .......... F25D 3/11; F25D 3/105; F25D 20/001; F25D 20/003; F25D 25/00; F25D 25/005;
(Continued)

(56) References Cited

U.S. PATENT DOCUMENTS 3,712,179 A * 1/1973 Hanson ................... F01B 11/04
91/220
4,157,018 A * 6/1979 Goltsos ................... A23L 3/361
62/373
(Continued)

OTHER PUBLICATIONS

Lee, H; et al. Article: Ultra-rapid vitrification of mouse oocytes in low cryoprotectant concentrations. Reproductive BioMedicine Online. 20, 201-208, Jan. 1, 2010. ISSN: 1472-6483.*

*Primary Examiner* — Justin Jonaitis
*Assistant Examiner* — Joel Attey
(74) *Attorney, Agent, or Firm* — Thibault Patent Group

(57) ABSTRACT

The present invention, in some embodiments thereof, relates to a method and scalable devices for hyperfast cooling and re-warming of samples. More specifically, it relates to cryogenic preservation of biological samples via vitrification. It includes: a liquid sample placed at ambient temperature in a flat thermo conductive container that in some embodiments additionally contains a detachable disposable or sterilizable thermo conductive spiral; transferring the sample to a cooling chamber using a linear percussion stepping motor drive; hyperfast cooling of the sample using streams of pressurized liquid coolant; transferring the sample to a detachable shipping/storage chamber filled with liquid coolant, from which the sample can be transferred to another vessel that contains liquid cryogenic coolant and moved back to the shipping/storage chamber. This chamber can be then attached to a re-warming chamber, in which the sample is heated to a biologically tolerant temperature above 0 degrees Celsius in a hyperfast manner.

7 Claims, 14 Drawing Sheets

(51) Int. Cl.
*F25D 3/11* (2006.01)
*F25D 25/00* (2006.01)
*F25D 13/06* (2006.01)
*G01N 1/42* (2006.01)
*F25D 25/04* (2006.01)

(52) U.S. Cl.
CPC ......... A01N 1/0257 (2013.01); A01N 1/0268 (2013.01); G01N 1/42 (2013.01); *A01N 1/0284* (2013.01); *F17C 2227/045* (2013.01); *F25D 3/105* (2013.01); *F25D 3/11* (2013.01); *F25D 13/06* (2013.01); *F25D 13/062* (2013.01); *F25D 25/00* (2013.01); *F25D 25/005* (2013.01); *F25D 25/04* (2013.01)

(58) Field of Classification Search
CPC ........ F25D 25/04; F25D 13/06; F25D 13/062; F25D 3/127; A01N 1/0236–1/257; A01N 1/0284; F17C 2227/045
USPC .......................................................... 62/51.1
See application file for complete search history.

(56) References Cited

U.S. PATENT DOCUMENTS

| | | | | |
|---|---|---|---|---|
| 4,403,479 | A * | 9/1983 | Rasovich | A23L 3/362 62/186 |
| 5,385,307 | A * | 1/1995 | Azar | B29B 17/0206 241/41 |
| 5,813,237 | A * | 9/1998 | Grace | A23L 3/362 62/374 |
| 6,019,997 | A * | 2/2000 | Scholz | A61K 9/0014 424/449 |
| 6,244,329 | B1 * | 6/2001 | Ullman | A01N 1/02 165/63 |
| 7,162,888 | B2 * | 1/2007 | Shu | B25J 11/00 378/208 |
| 7,197,884 | B2 * | 4/2007 | Jones | A01N 1/02 62/86 |
| 2007/0227719 | A1 * | 10/2007 | Voelker | G01N 1/31 165/256 |
| 2012/0255313 | A1 * | 10/2012 | Katkov | F25D 3/102 62/51.1 |

* cited by examiner

METHOD AND SCALABLE DEVICES FOR HYPER-FAST COOLING AND WARMING

TECHNICAL FIELD

The present invention, in some embodiments thereof, relates to hyper-fast cooling of samples. More specifically, the present invention relates to the cryogenic preservation of biological cells via cooling down to the liquid nitrogen temperature in medicine, animal husbandry, and biomedical science. Some embodiments relate to fast cooling of certain electronic equipments such as computer apparatuses, to fields in metallurgy for achieving the glassy state of metals and metals alloys, and to other related fields where hyper-fast cooling of small samples is desirable. More particularly, the invention relates to, but not limited to, devices and methods for hyper-fast cooling for vitrification of biological cells, which will be the major field discussed in the Application.

BACKGROUND OF THE INVENTION

Vitrification is a process when a liquid or semi-liquid biological sample becomes highly viscous, avoiding intracellular and intercellular ice formation and thus, increasing chances for survival; an amorphous vitreous (glassy) phase is formed. This glassy state may be achieved in most liquids by means of very fast cooling. Thus, for example, pure water vitrification is achieved at the cooling rate of about $10^8$ K/min. Utilization of cryoprotective agents (CPAs) significanty increases these extremely high cooling rates to rapid (higher 10,000° C Min) or ultra-rapid (ultra-fast) cooling rates (above 10,000° C/Min but below 100,000° C/Min). This method is very attractive for cryopreservation of biological samples. High concentrations of permeable CPAs must be used for the most widely used methods of equilibrium (slow) and quasi-kinetic vitrification with relatively more rapid rates of cooling, including ultra-rapid (higher than 20,000° C/Min but below 50,000° C/Min) vitrification. Those CPAs, used in equilibrium or quasi-kinetic vitrification, which comprise, but are not limited to, glycerol, [Katkov et al., 2012], can substantially damage the cells even without vitrification due to either osmotic damage or specific chemical toxicity [Katkov & Pogorelov, 2007; Katkov, 2011]. The Leidenfrost effect (LFE) is a vapor film formation (film boiling) on the site of the contact between the coolant/heater and heated/cooled sample. In the former case, there is heating LFE, which can be observed when a droplet of water is placed on overheated metallic pan. In the latter case, there is cryogenic LFE, when a liquid coolant boils and forms a vapor coating around the cooling sample (which can be both liquid or solid). It is the major factor that substantially impedes the rate of the surface cooling. All the devices referenced above where the samples are immersed into liquid nitrogen or other coolant, have substantially lower cooling rates than as claimed because of the cryogenic LFE.

It would therefore be advantageous to reduce the LFE effect, to improve the efficiency of cooling, and to simultaneously reduce the need for toxic CP As. Some embodiments of the present invention can achieve these goals with hyper-fast cooling rates (50,000° C/Min and higher) by reducing the LFE effect, and by totally eliminating or substantially decrease the use of potentially toxic permeable CPAs mentioned above.

Another goal of this invention is to insure hyper-fast re-warming of the vitrified samples and avoid the re-crystallization or the growth of new crystals during warming of the kinetically vitrified sample

BRIEF SUMMARY OF EMBODIMENTS OF THE INVENTION

In accordance with present invention here is the method of specimen hyper-fast cooling and heating using cryogenic refrigerant, comprising
a) transfer of container with biological specimen under power pulse action from environment temperature zone to cooling vessel, which jets effecting at least one surface, for example bottom surface, of flat-ended container, are inclined; b) transfer of container with biological specimen under power pulse action from atomized flow of liquid cryogenic refrigerant of cooling vessel to neighboring storage vessel, prefilled with liquid cryogenic refrigerant; c) transfer of flat-ended container with biological specimen under power pulse action from neighboring storage vessel to active zone of heating device; d) flat-ended container with biological specimen is transferring with high speed intermittently under action of power pulses sequence; e) a sequence of short power pulses, which are separated by prolonged intervals, is created with percussion motor drive.

In present method hyper-fast cooling rates of biological specimen in flat-ended container are being created. Its achieved by fast transfer of mentioned container from environmental temperature zone to cooling vessel, where is goes under the upward blast of atomized liquid cryogenic refrigerant. Where liquid refrigerant jets, affecting bottom surface of flat ended container, are inclined.

As mentioned flow of liquid nitrogen is effecting at least one surface, for example, bottom surface of flat-ended container at an angle, the vapor film of gaseous nitrogen formed initially at the contact boundary of container and liquid nitrogen will be pervaded by liquid nitrogen jets and reflected inclined, pushing gaseous cryogenic refrigerant back from the container and not preventing further liquid nitrogen jets contact with container surface. Atomized liquid refrigerant with its jets are intensively effecting all areas on container bottom surface, cooling them simultaneously, which almost eliminates spatial temperature gradient on the flat-ended container surface and encourages high cooling rates.

Slop angle of flat-ended container toward horizontal plane or jets is 5-45°, which makes gaseous film of evaporated nitrogen on the flat container surface removal most efficient.

After cooling, container is transferred to storage vessel, prefilled with liquid cryogenic refrigerant from neighboring cooling vessel under power pulse action. Since mentioned vessels are neighboring, container temperature remains almost the same. This allows container to stay in storage vessel in liquid refrigerant environment for a long time with little energy consumption. Mentioned vessel can be transferred on long distances, allowing regular topping up with refrigerant.

If necessary, hyper-fast heating of biological specimen from cryogenic temperature to environment temperature can be achieved by container's transfer from neighboring storage vessel to heating vessel located in environment temperature zone. With that HP magnetic field of storage vessel is effecting biological specimen located in the container, encouraging its rapid and uniform heating.

Since container is transferring intermittently under action of power pulses sequence, then during prolonged pause between pulses, container spatial fixation occurs in every vessel. Most efficient for practical use is container's transferring in one direction, which provides by linear percussion stepping motor drive. High speed of container transfer is achieved by power pushing pulses. Container transfer is accompanied by opening of located on vessel wall heat insulating curtains, when container pushes them.

In accordance with present invention here is the device of specimen hyper-fast cooling and heating, using cryogenic refrigerant, comprising:

a) percussion motor drive located in environment temperature zone, with guide pin, which provides stepwise, interrupted by prolonged intervals, high speed transfer of flat-ended container with biological specimen; b) neighboring to each other, nozzle with atomizer on its end in cooling vessel, providing directed flow of liquid cryogenic refrigerant, which jets affecting at least one flat surface, for example bottom surface of flat-ended container, are inclined, and storage vessel with liquid cryogenic refrigerant; c) neighboring to each other storage vessel with liquid cryogenic refrigerant and active zone of heating device; d) containment vessel with liquid cryogenic refrigerant, at the top part of which, heater and excessive pressure release valve connected to cooling vessel with heat-insulated nozzle with a shutoff valve, are located.

Linear percussion stepping motor drive can be made as coaxial linear pulse electric motor of induction type, containing fixed inductor, ignited from capacitive energy storage, and electro conductive anchoring block pressed to inductor by pullback spring, providing transferring with guide pin stops.

Linear percussion stepping motor drive can be made as coaxial starter of telescopic type, consisting of encasing each other cylinders, spring-assisted from the end vertical part of guide support, cylinders are equipped with controlled clamps of compressed spring, internal cylinder is made as guide pin, and external cylinder is mounted on guide support, secured on the external wall of cooling vessel.

Guide pin connects to the container with ball clamp. Cryogenic liquid refrigerator is liquid nitrogen. Container looks like flat panel box, which bottom panel is thin made from heat conductive material, and top cover is made from optically transparent material. On the vessel side walls optically transparent vacuum windows are installed. Heat insulating curtains have split for guide pin. Storage vessel contains container holding system. Heat insulating curtains are made from solid, plastic foam. In cooling vessel above the atomizer with an opportunity of transferring the container with biological specimen, liquid cryogenic refrigerant jet deflector is installed. Guide pin is made from heat insulating material. Cooling and storage vessels are equipped with nozzles for gaseous cryogenic refrigerant outlet. Containment vessel with liquid cryogenic refrigerant is located lower than the level of cooling and storage vessels.

Guide pin, located in inner split of anchoring block, contains row of distributed along the axis elastic stops, pressed by neighboring with anchoring block power disk, while transferring under action of pullback spring towards guide pin.

Inductor is made in the shape of solid, multi stranded disk coil, impregnated with epoxide compound, with inner split for guide pin.

Electro conductive anchoring block is made in the shape of copper disk with inner split for guide pin and outer diameter matching outer diameter of inductor. Bottom part of container is made from copper or other highly thermo conductive but biologically neutral material. Top cover of the container is made from thermal glass.

Excessive pressure releasing valve of containment vessel contains operation level adjustment, valves outlet is connected to the pipeline, which end is located in environment temperature zone, outdoors with device for hyper-fast cooling and heating of specimen.

Outlets for release of gaseous cryogenic refrigerant from cooling vessel are connected to storage vessel by pipeline, which end is located in environment temperature zone, outdoors with device for hyper-fast cooling and heating of specimen.

In present device hyper-fast cooling and heating rates for biological specimen located in the flat ended container are created by means of linear percussion stepping motor drive with guide pin, which provides stepwise, interrupted by prolonged intervals, high speed linear transfer of container with biological specimen from one zone to another, with temperatures that differs wildly. Drive component located in environment temperature zone provides maximum simplicity and functioning reliability.

Because cooling, storage and heating vessels are located along container with biological specimen moving direction, present device is the most simple and reliable, eliminating undesirable temperature gradient between vessels, which would be unavoidable if there were splits between vessels, for example with environmental temperature.

Presence of nozzle with atomizer on its end provides liquid cryogenic refrigerant upflow. Upflow jets intensively effecting bottom panel of container, which were quickly transferred from environment temperature zone. Since refrigerant jets are inside the cooling vessel, which doesn't have excessive pressure, so these jets temperature is not rising compare to the boiling temperature of refrigerant with atmosphere pressure.

Presence of container holding system in storage vessel allows to transport mentioned vessel on significant distances, providing rapid container exit to heating vessel with HP magnetic field. Because of indicated factors high speed of biological specimen heating is provided.

Pressure sealed vessel with liquid cryogenic refrigerant at different moments of working process is functioning as source or receiver of liquid refrigerant for cooling and storage vessels. It's possible because of the heater, excessive pressure release valve and insulated nozzles with shutoff valves connected to cooling vessel and storage vessel.

For functioning as source of liquid refrigerant, vessel is getting pressure sealed by shutting all valves and turning the heater on, and after matching shutoff valve gets opened and refrigerant enters the cooling or storage vessel.

For functioning as a receiving device for liquid refrigerant, excessive pressure release valve is to be opened after which proper shutoff valve is to be opened and refrigerant is coming from cooling vessel or from storage vessel entering pressure sealed vessel. For this purpose pressure sealed vessel is located lower the level of cooling and storage vessel. Because of pressure sealed vessel location, device is compact with minimal length of insulating nozzles. Function of receiver of liquid refrigerant allows to reuse it, pump under pressure to upper vessels (cooling and storage) and discharge to located beneath pressure sealed vessel.

Presence of release valves for gaseous cryogenic refrigerant outlet from cooling and storage vessel eliminates excessive pressure in them.

Presence of heat insulating curtains, located on the vessel walls along container moving direction, allows to open them, moving container pressure. Curtain opening occurs by turn around horizontal axis, located above each curtain. Presence of splits in curtains allows the guide pin go through them, ensuring closing the curtain. Besides, splits provide fixation of guide pin located inside of them by heat insulating curtain.

Thick plastic foam used for heat insulating curtains makes them light, cheap and mechanically strong while remaining good heat retention.

Performing linear percussion stepping motor drive as coaxial linear pulse motor drive of induction type allows automates the device and make it convenient in service.

Performing inductor as solid multistranded disk coil, impregnated with epoxide compound, with inner split for guide pin makes electro motor device reliable, functional and efficient. For the same purpose conductive anchoring block is made in the shape of copper click with inside split for guide pin and outer diameter, matching outer diameter of inductor.

Row of distributed along the axe elastic stops, pressed by power dick, neighboring with anchoring block, helps guide pin increment, located inside anchoring block split, and spatial fixation of container in desired place, while their transferring under pullback spring action against guide pin. Specified power disk provides anchoring block shape retention, which is made from brittle electro-conducting material, force transfer on pullback spring and mechanical exchange with elastic stops.

Performing described motor drive as coaxial starting device of telescopic type, makes device simple and operationally reliable. Presented telescopic device is characterized by long length and small cross dimensions, providing discrete (stepwise) length extension while pullback spring is effecting matching controlled clamp.

Connection of guide pin and container with ball clamp allows theirs fixation at required angle against each other. Since fixation angle can be adjusted, high cooling rate of biological specimen with different thickness and composition can be achieved.

Using liquid nitrogen as cryogenic liquid refrigerant makes the device cheap, safe, and reliable while still providing high cooling and heating rate for biological specimen.

Performing container in a shape of flat box allows easily place sizable biological specimen in any condition (hard, jelly-like, liquid and others) in it. Performing bottom panel of container thin from heat conductive material allows to cool the specimen efficiently. Most available heat-conductive material is copper.

Performing cover lid of container from optically transparent material allows visual control of biological specimen vitrification process. Optically transparent vacuum windows, installed on the vessels side walls serve the same purposes. Most available and efficient material for windows covers is thermal glass.

Presence of liquid cryogenic refrigerant flow jets deflector in cooling vessel allows to perform top cover of cooling vessel light and not impacted by refrigerant strong flow with container absence between atomizer and deflector. The deflector concentrates mechanical power of liquid nitrogen in small volume.

Performing guide pin from heat-insulating material, such as glass fiber plastic, for example—strong material, resistant to temperature gradient, protects it from heat flow coming from areas with different from container temperature, which helps its thermal state retention.

Making cooling and storage vessels from heat-insulating material helps to keep required temperature in them and liquid nitrogen preservation by small heat flow coming through walls. The simplest, most reliable and available material is solid plastic foam.

Presence of operation level adjustment in excessive pressure releasing valve, allows controlling refrigerant pressure tolerance in containment vessel, preventing its mechanic damage.

Connection of excessive pressure releasing valve outlet in containment vessel, outlets for gaseous cryogenic refrigerant release from cooling vessel and storage vessel with pipeline, which end is located in environment temperature zone outdoors with device for hyper-fast cooling and heating of specimen allows release of gaseous nitrogen from indicated building, providing safe atmosphere for maintenance staff.

In heating device may contain HP magnetic field source or hot compressed gas.

Percussion drive motor can provide linear and rotation motion, which simplifies the design of device vessels. With that, forming atomizer nozzle jets of cooling vessel are installed at an angle to the atomizer surface, which located parallel to the surface of a flat-ended container.

DETAILED DESCRIPTION OF THE PREFERRED EMBODIMENTS OF THE INVENTION

Figure 1:
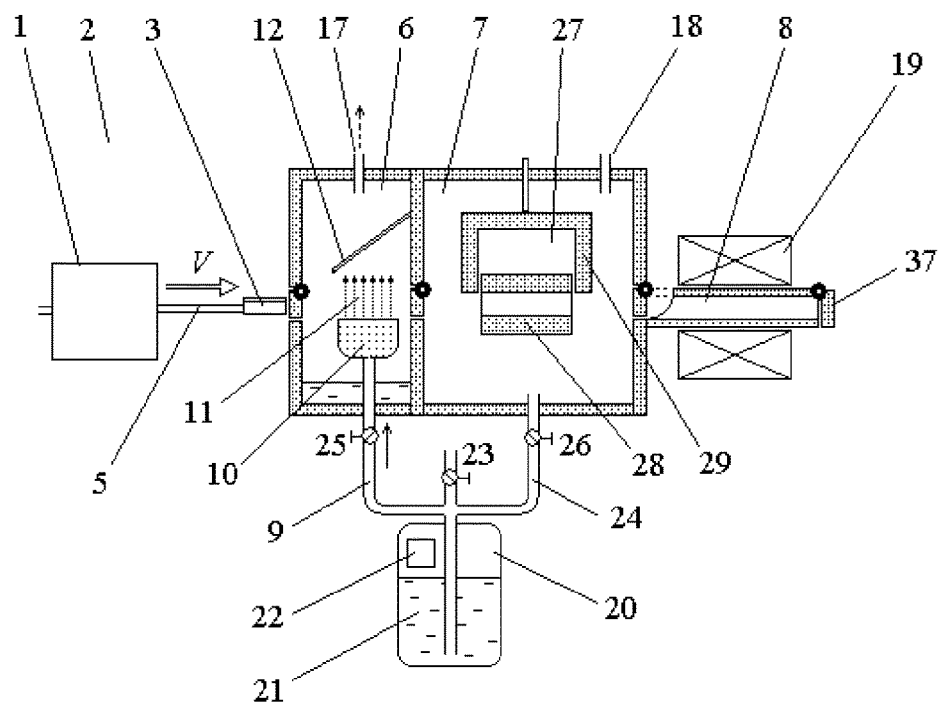
FIG. 1—is a perspective view of a device for hyper-fast cooling and heating of specimen using cryogenic refrigerant and linear percussion stepping motor drive before placing container in cooling vessel (without side walls). Solid, thin, arrow shows liquid nitrogen moving direction, dashed thin arrow—gaseous nitrogen moving direction, and thick arrow—guide pin with container moving direction at the speed V.

Presented device can be made using a linear percussion stepping motor drive and using a motor drive which provides linear and rotary motion.

Consider a device that uses linear percussion stepping motor drive.

Presented device of specimen hyper-fast cooling and heating, using cryogenic refrigerant consists of linear percussion stepping motor drive 1, located in zone 2 with environment temperature, container 3 with biological specimen 4, which is connected to motor drive 1 by guide pin 5. Along the container 3 moving direction at the speed V, contiguous with each other cooling vessel 6 and storage vessel 7 and active zone of heating device 8 are located. Adjacency is achieved by mentioned vessels sharing the same walls. Vessels 6 and 7 are made from heat insulating material, like solid plastic foam, for example.

In cooling vessel 6 nozzle 9 with atomizer 10 on its end is installed, providing upflow jets 11 of liquid cryogenic refrigerant, such as liquid nitrogen for example. Above atomizer 10 flow jets deflector 12 is secured, so there is an opportunity of non-contact transfer and locating container 3 between atomizer 10 and deflector 12.

Container 3 is performed in the shape of flat box, which bottom panel 13 is thin and made from heat conductive material, such as copper, for example, and top cover 14 is made of optically transparent material. Guide pin 5, made from heat insulating material, such as glass fiber plastic, connected to container 3 by ball clamp 15.

Figure 12:
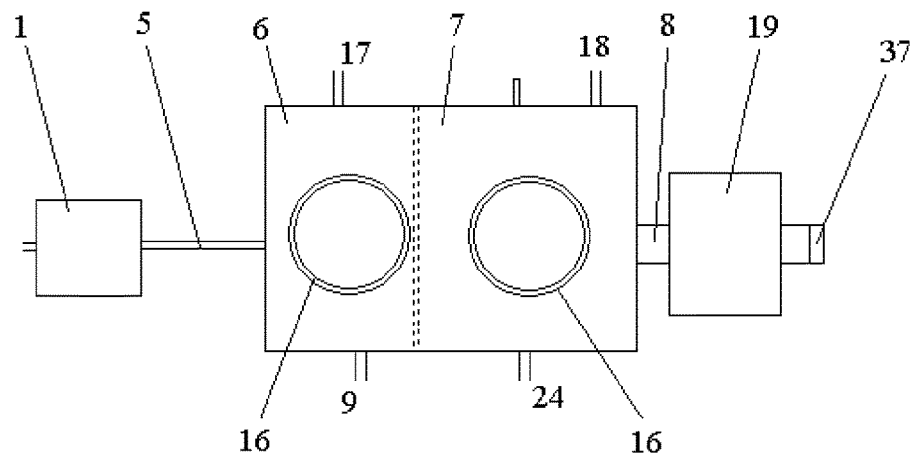
FIG. 12—is a side view of specimen hyper-fast cooling and heating device with side walls.

On the side walls of cooling vessel 6 and storage vessel 7 optically transparent vacuum windows 16 are installed (FIG. 12). Upper cover (lid) 14 of container 3 can be made from thermal transparent glass, thermal "memory" plastics, or highly thermoconductive material. Windows 16 are be made from thermal transparent glass. Cooling vessel 6 and storage vessel 7 are equipped with nozzles 17 and 18 respectively, for gaseous nitrogen outlet.

Heating device, located in zone 2 with environment temperature, contains source of HP magnetic field 19, covering inside space of mentioned device.

Lower the level of cooling vessel 6 and storage vessel 7, containment vessel 20 with liquid nitrogen 21 is located. Vessel 20 is made as cryostat, withstanding increased internal pressure.

At the top part of vessel 20, heater 22, excessive pressure release valve 23, and insulated nozzles 9 and 24 connected to vessels 6 and 7 respectively are located. On nozzles 9 and 24 shutoff valves 25 and 26 are installed respectively. Heater 22 can be electric for example with controlled intensity of current.

Excessive pressure releasing valve 23, is equipped with operation level adjustment (not shown on the drawing), which allows to control pressure tolerance of refrigerant in containment vessel 20, preventing its mechanic damage from extremely high pressure.

Outlet of valve 23, valve 17 of cooling vessel 6 and outlet 18 of storage container 7 are connected to pipeline (not shown on the drawing), which end is located in environment temperature zone outdoors (not shown on the drawing), where device for hyper-fast cooling and heating of specimen is located. It allows to discharge gaseous nitrogen from vessel 6, 7 and 20 to environment, instead of indoors, providing safe atmosphere for maintenance staff.

Storage vessel 7 contains holding system 27 for container 3, including fixed part 28 and moving part 29.

Figure 2:
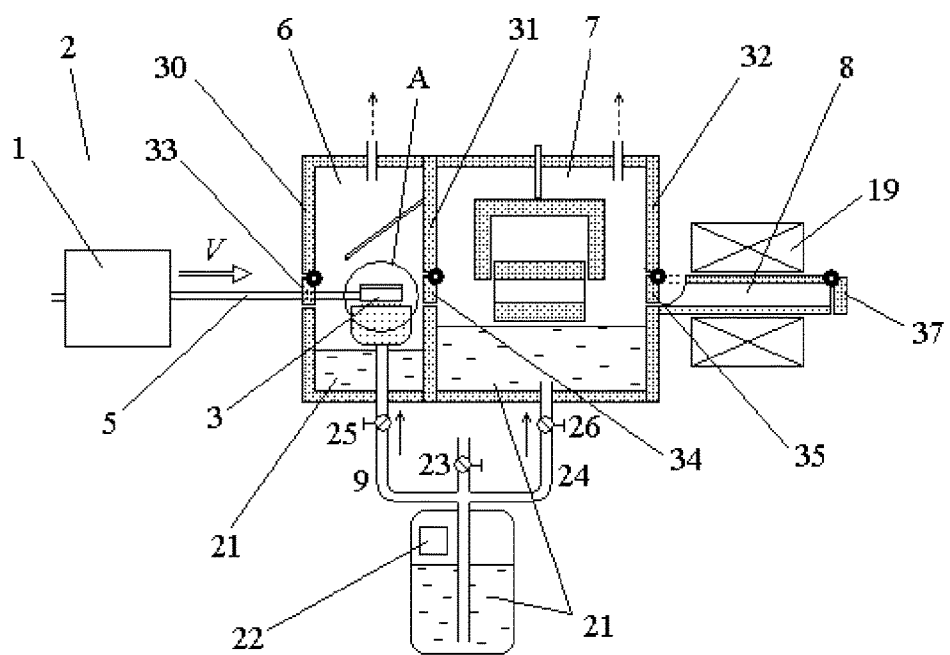
FIG. 2—is a device on FIG. 1 at the moment when container is placed in cooling vessel.
Figure 11:
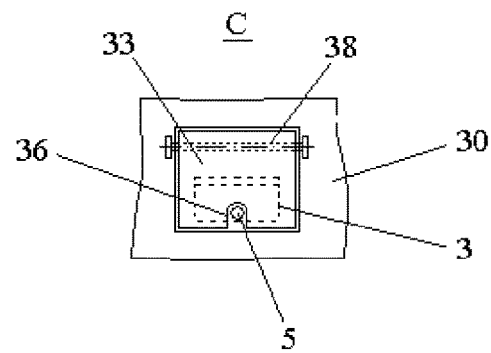
FIG. 11—is a view C on FIG. 10.

On vertical walls 30, 31, and 32 of vessels 6, 7 and 18 along moving direction of container 3 at the speed V, heat insulating curtains 33, 34 and 35 are located respectively (FIG. 2). Mentioned heat insulating curtains are made of solid plastic foam with split 36 for guide pin 5 (FIG. 11). On the end of heating vessel 8 outlet curtain 37 is located. All heat insulating curtains, such as 33 for example, are installed with ability to turn around horizontal axis 38, located above curtain and secured on the wall 30 of vessel 6 when container 3 is effecting it (FIG.8—FIG. 11).

Figure 13:
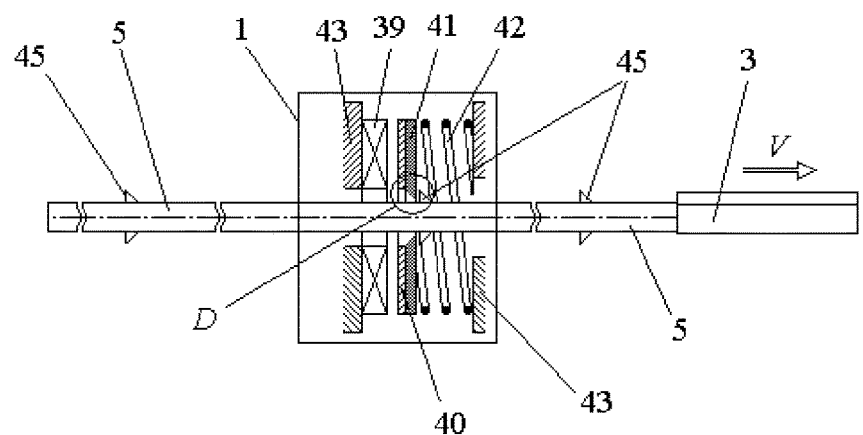
FIG. 13—is a schematic view of a linear percussion stepping motor drive performed as coaxial linear pulse motor drive of induction type.

FIG. 13 presents linear percussion stepping motor drive 1 made as coaxial linear pulse motor drive of induction type. This motor drive contains fixed inductor 39, ignited from capacitive energy storage (not shown on the drawing), electro-conductive anchoring block 40, power click 41, connected to the anchoring block and pullback spring 42. Inductor 39 and spring 42 are attached to fixed base 43, which is interrelated with guide support 44.

Figure 20:
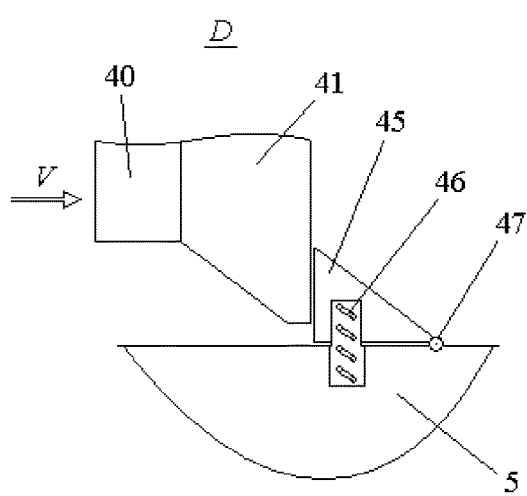
FIG. 20—is a view D on FIG. 13 in initial state.
Figure 21:
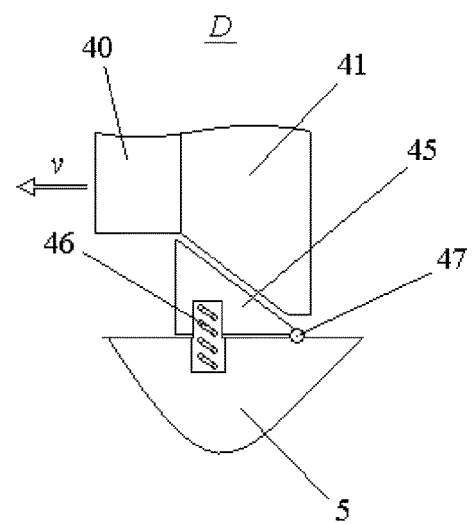
FIG. 21—is a view D on FIG. 13 at the moment of power disk movement with anchoring block under pullback spring pressure at the speed v.
Figure 22:
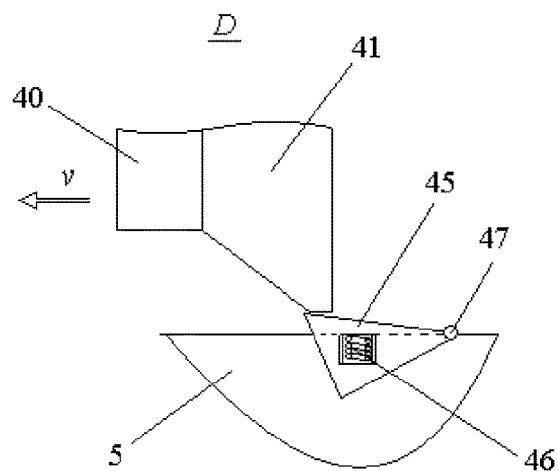
FIG. 22—is a view D on FIG. 13 at the moment of power disk movement with anchoring block under pullback spring pressure at the speed v.

Inside internal openings of inductor 39, anchoring block 40 and power disc 41, guide pin 5 is located, containing row of distributed along the axis elastic stops 45, made with ability to be compressed by power disc while moving under pullback spring 42 pressure. Elastic stop 45, having triangle shape in section for example, connected to guide pin 5 with spring 46, contiguous to its vertical side, and to axis 47, located on the corner of the moving direction of container at the speed V (FIG. 20—FIG. 22)

Inductor 39 is performed as solid multistranded disk coil, impregnated with epoxide compound. Conductive anchoring block 40 is made in the shape of copper click with outer diameter, matching outer diameter of inductor 39. Power disc 41 is made of sound material such as stainless steel with outer diameter, matching outer diameter of anchoring block.

Figure 14:
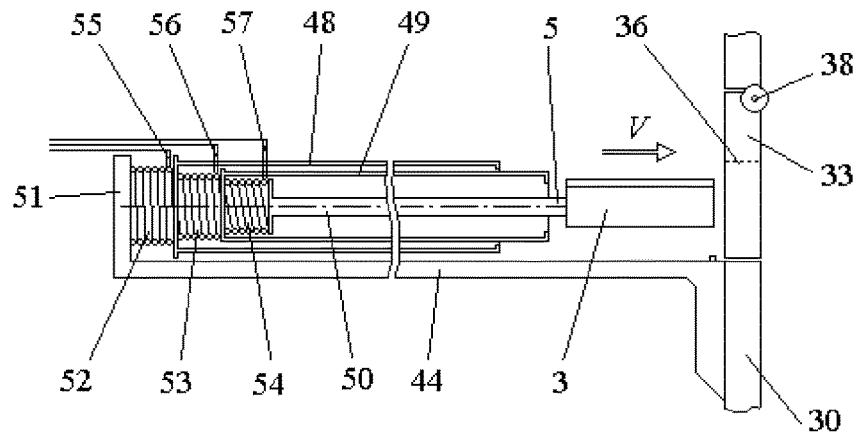
FIG. 14—is a schematic view of a linear percussion stepping motor drive performed as three-section coaxial starter device of telescopic type in initial (compressed) condition.
Figure 15:
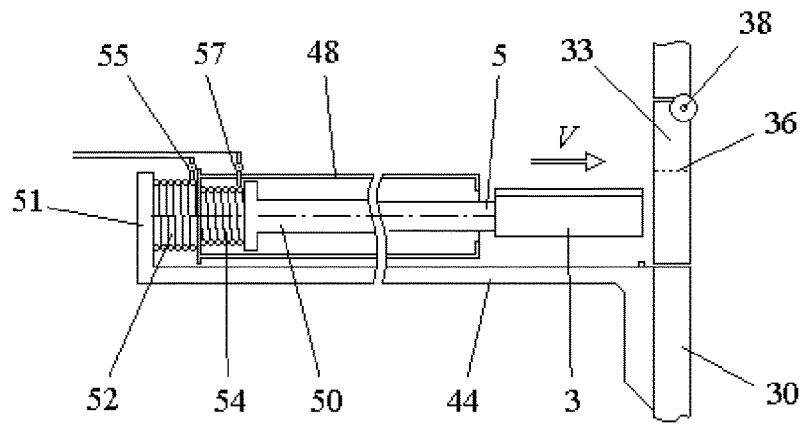
FIG. 15—is a schematic view of a two-section coaxial starter device of telescopic type in initial (compressed) condition.

On FIG. 14 and FIG. 15, linear percussion stepping motor drive 1 is presented, which is made as three and two sectioned respectively coaxial starter device of telescopic type. Three sectioned starter device (FIG. 14) consists of encasing each other cylinders—external 48 intermediate 49, and internal 50. At the same time internal cylinder 50 made as guide pin 5. External cylinder 48 is installed on the guide support 44, which is secured on the outer wall 30 of cooling vessel 6. Guide support has tail vertical piece 51. Between tail vertical piece 51 of guide support 44 and front piece of external cylinder 48 spring 52 is located. Between front pieces of external 48 and intermediate 49 cylinders spring 53 is located. Between front pieces of intermediate 49 and internal 50 cylinders spring 54 is located. Every spring 52, 53, and 54 has controlled clamps, 55, 56 and 57 respectively, keeping them in compressed condition.

Two sectioned starter device (FIG. 15) consists of encasing each other external 48 and internal 50 cylinders. Internal cylinder 50 is made as guide pin 5. External cylinder 48 is installed on guide support 44, which is secured on the outer wall 30 of cooling vessel 6. Guide support has tail vertical piece 51. Between tail vertical piece 51 of guide support 44 and front piece of external 48 and internal 50 cylinders spring 54 is located. Each spring 52 and 54 has controlled clamps, 55 and 57 respectively, keeping them in compressed condition.

Figure 19:
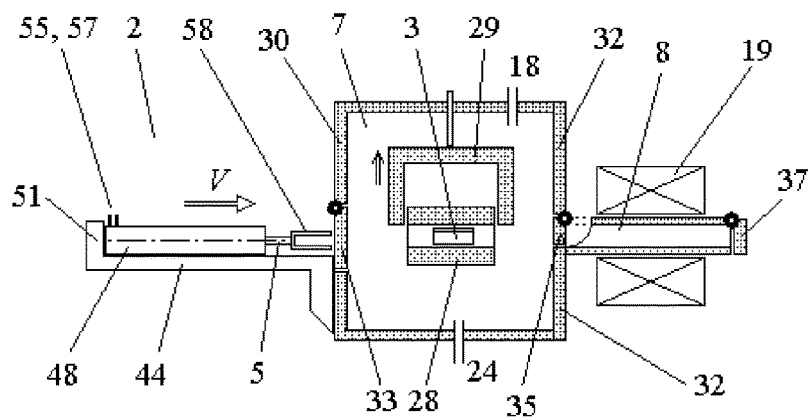
FIG. 19—is a schematic view of specimen storage and hyper-fast heating device and coaxial starter device of telescopic type.

FIG. 19 presents specimen storage and hyper-fast heating device using cryogenic refrigerant and coaxial two sectioned starter device of telescopic type, which has clamp 58 at the guide pin end for container 3, located in storage vessel 7.

Consider a device of specimen hyper-fast cooling and heating, using motor drive which provides linear and rotary motion (FIG. 23-36).

A device of specimen hyper-fast cooling and heating, using cryogenic refrigerant consists of motor drive 1, which provides linear and rotary motion, located in zone 2 with environment temperature, container 3 with biological specimen 4, which is connected to motor drive 1 by guide pin 5

Figure 24:
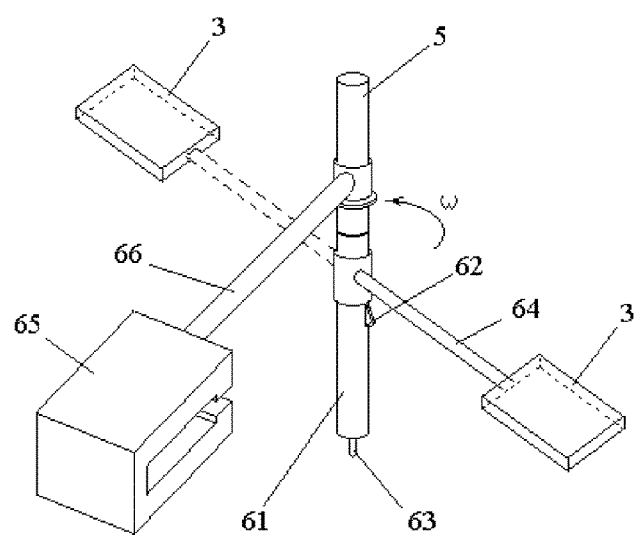
FIG. 24—is a general view of guide pin with container and heat-insulated capsule on FIG. 23.

Guide pin 5 is introducing into cooling vessel 6 via split/hole (not shown on the drawing) which shuttled off with moving heat insulating curtain 59 at its/cooling vessel's cover lid 60. A sectional end unit 61 is installed with elastic clamps 62 at the end of pin 5. Central pivot/rod 63 of guide pin 5 is located in central split/hole (not shown on the drawing) of end unit 61 with a ledge beyond/outside its end surface (FIG. 24). Central pivot/rod 63 hold elastic clamps 62 in release state.

Container 3 is connected to the sectional end unit 61 of guide pin 5 with a bar 64 with ability of mutual transferring, for example in axial direction. To the guide pin 5 connects a heat insulating capsule 65 meant for encasing /to encase of container 3 and made from plastic foam for example, with a bar 66 with ability of mutual transferring.

Figure 30:
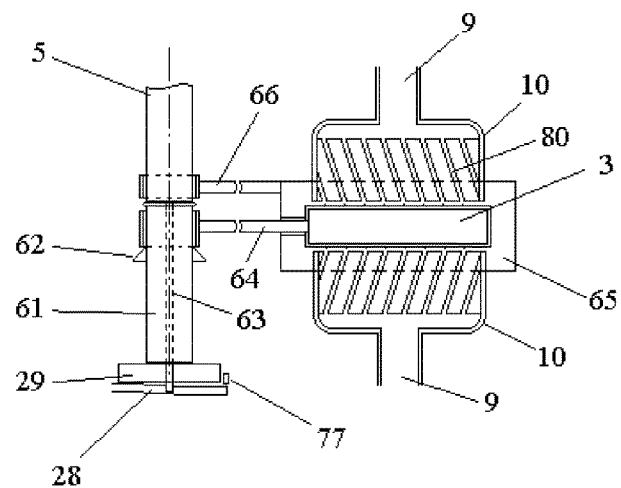
FIG. 30—is a device on FIG. 29 with guide pin and container located in zone of cryogenic refrigerant jets atomizers.

Cooling vessel 3 is equipped with nozzle 17 for gaseous nitrogen outlet. Inside cooling vessel 6 nozzle 9 is installed, with two opposite atomizers 10 on its end with gap for non-contact transfer container 3. Flat-ended container 3 in gap is encasing from opposite sides by two atomizers 10, the distance between them is less than matching dimensions of heat insulation capsule 65 (FIG. 30).

Container 3 is performed in the shape of flat-ended box which panels are thin and made from heat conductive material, such as copper, for example (FIG. 24).

Nozzle 9 with a shutoff valve 25 is going out of pressure-tight vessel 20, which is made as cryostat, withstanding increased internal pressure, with liquid nitrogen 21. At the top part of vessel 20, heater 22, increased pressure of gaseous nitrogen release valve 23 are located. Valve 23 is equipped with operation level adjustment (not shown on the drawing), which allows to control pressure tolerance of gaseous refrigerant in containment vessel 20, preventing its mechanic damage from extremely high pressure.

Valves outlet 23 is connected to the pipeline 67, which end is located in environment temperature zone, outdoors (not shown on the drawing) with device for hyper-fast cooling and heating of specimen. It allows to discharge gaseous nitrogen from vessel 20 to environment, instead of indoors, providing safe atmosphere for maintenance staff.

Lower the level of cooling vessel 6, cryogenic vessel 68, Dewar vessel for example, is installed, for discharge liquid refrigerant 21 from vessel 6 with nozzle 69, which determines the level of liquid refrigerant in vessel 6, and nozzle 70 with valve 71, meant for complete discharge liquid refrigerant 21 from vessel 6.

Storage vessel 7 can be installed both inside cooling vessel 6 (FIG. 23, 25) and heating vessel 72.

Figure 27:
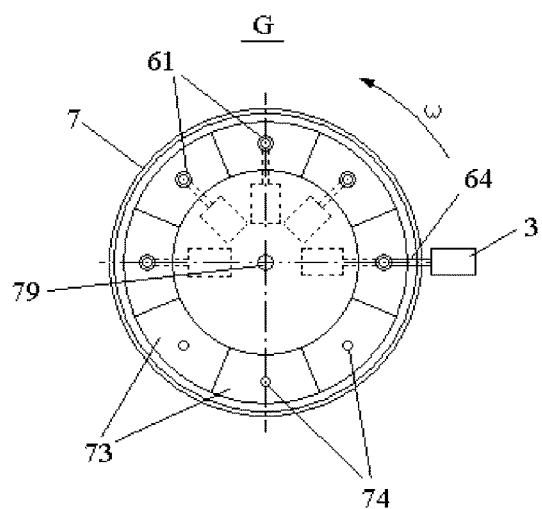
FIG. 27—is a view G on FIG. 23.
Figure 28:
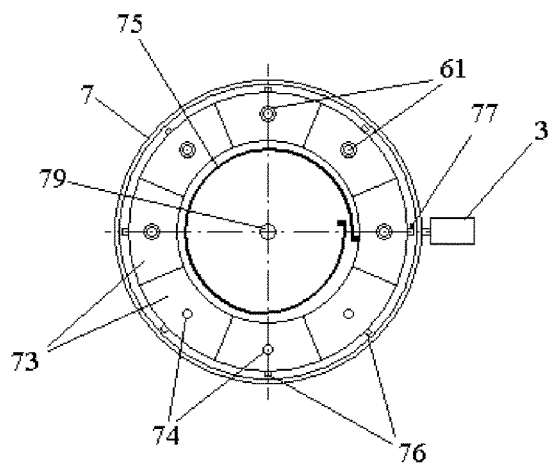
FIG. 28—is a device on FIG. 27 with spring and props of moving part of containers holder.

Vessel 7 contains holding system 27 for container 3, which includes fixed 28 and moving 29 units. Moving unit of holding device 27 consists of sections 73 with spot splits 74 for end units 61 of guide pin 5 (FIG. 27). Mutual transferring sections 73 of moving unit 29 towards fixed unit 28 realizes with spring 75 (FIG. 28). Increment transferring sections 73 executes with stops 76 mounted on them, which interact stop 77, which is located on fixed unit 28 of holding device 27 (FIG. 30 and FIG. 28). Stop 77, under effect central pivot 63 of guide pin 5, is pressed down and releases matching stop 76 of section 73.

Figure 26:
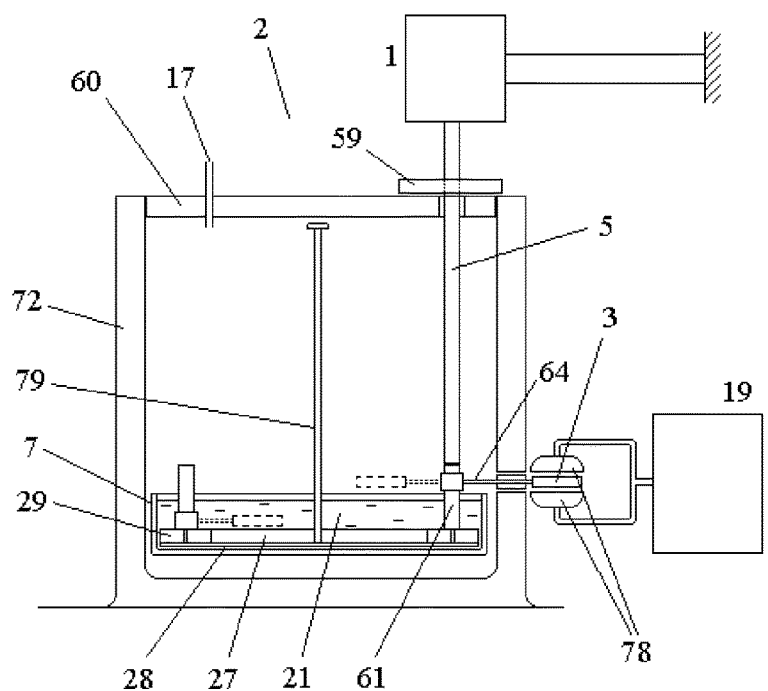
FIG. 26—is a device on FIG. 23 after placing container in active zone of heating device.

Inside heating vessel 72 two elements 78 of heating device 19 are located with gap for non-contact transfer container 3 (FIG. 26). Heating device 19 may contain HP magnetic field source or hot compressed gas.

Storage vessel 7 contains handle 79, which allows place and take out the vessel both in cooling vessel 6 and in heating vessel 72.

Figure 29:
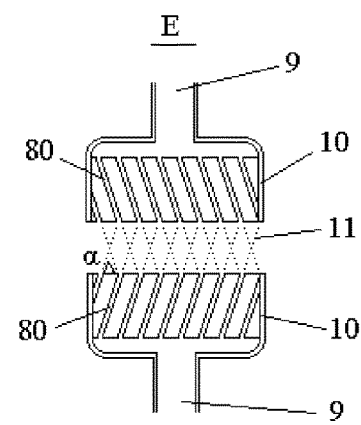
FIG. 29—is a view E on FIG. 23.

Guide nozzles 80 of atomizer 10 which are forming liquid refrigerant jets 11, are installed at the angle a to the atomizer surface, located parallel to the surface of a flat-ended container (FIG. 29).

Figure 37:
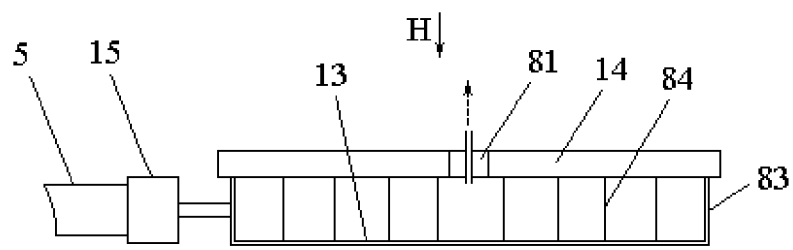
FIG. 37—side view of a container with a thermoconductive spiral inside.

Container 3 (FIGS. 37-39) has an outlet valve 81, which as one of the embodiments can be located on the center of upper cover (lid) 14, and inlet valve 82, which as one of the embodiments can be located inside wall 83 of the container 3. A spiral 84 made of a highly conductive but biologically neutral material such as copper is located inside the container 3 with its edges hermetically connected with the bottom of the container 13. and the upper cover (lid) 14.

Space between the turn of spiral 84 can be filled with the liquid specimen 4 with the syringe 85, the end (or a needle) of which can be inserted in the container through the inlet valve 81, which can containe self-sealing material such as a resin or rubber. The upper cover (lid) 14 of the container 3 is hermetically connected with the side walls of the container 83 hermetically. In one of embodiments, the upper cover (lid) 14 can be made of a "smart material" with an alloy opr plastic with thermal shape memory. The upper cover (lid) can be easily removed in working ambient but self-sealed hermetically with the walls at if cooled below the transition point.

Figure 38:
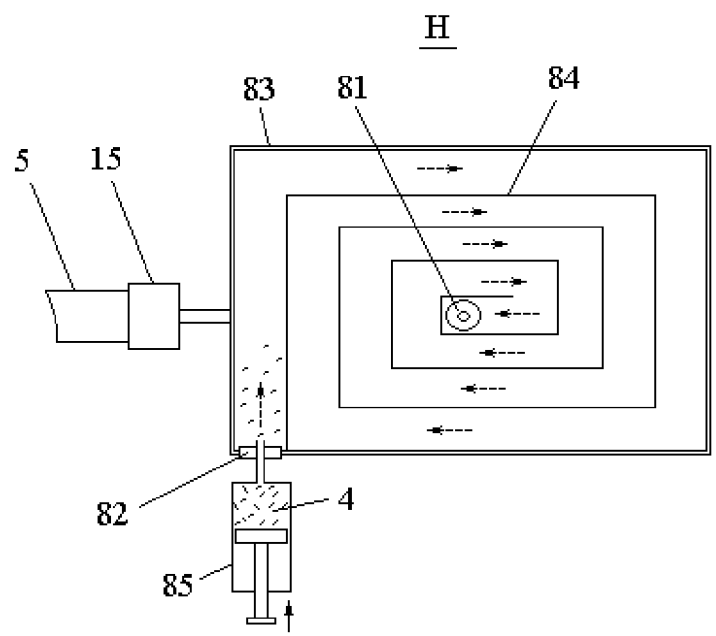
FIG. 38—is a view H on FIG. 37.
Figure 39:
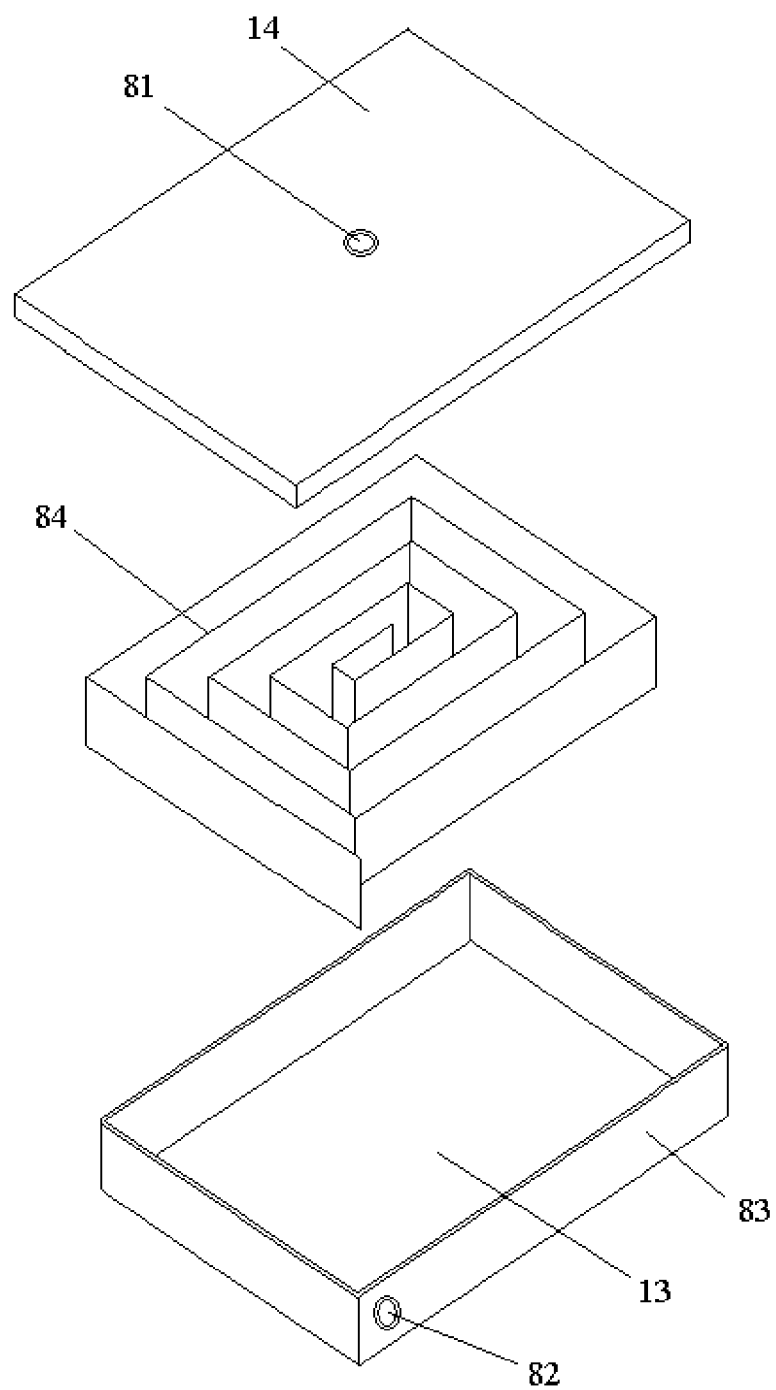
FIG. 39—is a general view of the upper cover (lid) container, highly thermo conductive spiral and the container for liquid specimens.

The filling of the container 3 can be made as following: The end (or needle) of the syringe 85 filled with liquid specimen 4 is placed into the inlet valve 82 (FIG. 38). The specimen 4 is pushed out to the outer turn of the spiral and moves further until all space in the spiral (the turns of which are shown in dotted lines is fully filled and the air/gas is displaced by exiting the outlet valve 81. After the all inter spiral space is filled, the syringe is removed and the specimen is fully isolated from outer space insuring sterile conditions inside the system. All elements of the system can be either disposable or sterilizable. The bottom of the container and/or its walls 83 can be made of either metals, alloys or high thermally conductive plastics/polymers.

Device using linear percussion stepping motor drive (FIG. 1-FIG. 22) works as follows:

Linear percussion stepping motor drive 1 is to be initialized.

If mentioned motor drive 1 is made as coaxial linear pulse motor drive of induction type (FIG. 13) conductive anchoring block 40 by means of power disc 41 with the help of pullback spring 42 is to be pressed to inductor 39. Elastic stop 45, by spring 46 is pulled out over guide pin 5 surface and power disc 41 is interacted with vertical side of stop 45 (FIG. 20).

Capacitive energy storage is to be charged.

If indicated motor drive is performed as coaxial starter device of telescopic type, for example tree sectioned (FIG.14), external 48, intermediate 49 and internal cylinder 50 are encasing each other. With that springs 52, 53 and 54 are being compressed and held by controlled clamps, 55, 56 and 57 respectively.

In two section coaxial starter device of telescopic type (FIG. 15) external 48 and internal cylinder 50 are encasing each other. With that, springs 52 and 54 are being compressed and held by controlled clamps, 55 and 57 respectively.

In initial condition shutoff valves 25, 26 and releasing valves 23 are to be closed, to provide sealing of the vessel 20 with liquid nitrogen 21. After, electric heater 22 is to be turned on, which leads to increased evaporation of liquid nitrogen and pressure increase of gaseous nitrogen in sealed vessel 20.

In environment temperature zone 2, container 3 is getting prepared. For this biological specimen 4 is placed in flat box with bottom panel 13, which is tightly closed by cover lid 14. Then container is to be connected to guide pin 5 (FIG. 5) end with ball clamp 15 at the angle $\alpha=5\text{-}45°$ between horizontal surface and bottom panel 13 of container (FIG. 6).

After this, shutoff valve 25 is to be opened. Under increased pressure of gas in sealed vessel 20 liquid nitrogen 21 is going through nozzle 9 under head, coming out of atomizer 10, entering cooling vessel 6. At first in gaseous state, then in a form of jets 11, liquid nitrogen flow is affecting flow deflector 12, which receives their mechanical energy. Evaporated gaseous nitrogen is going out through nozzle 17 from cooling vessel 6 to environment temperature zone 2, ensuring remaining of atmosphere pressure in vessel 6.

Process of liquid nitrogen jets 11 appearing can be watched through vacuum window 16, installed on the side wall of cooling vessel 6 (FIG. 12). Because of the vacuum between double thermal glass of the window sweating isn't occurring, due to condensation of moisture from environment temperature zone.

After linear percussion stepping motor drive 1 is initiated.

If motor drive is performed as coaxial linear pulse motor drive of induction type (FIG. 13), then upon the starter signal on electronic switch, such as thyristor for example (not shown on the drawing), discharging of charged upfront capacitive energy storage is conducted on inductor 39, where current excites whirling currents by magnetic field in electro conductive anchoring block 40. Created in this conditions repulsion is pushing anchoring block 40 together with power disc 41 off of fixed inductor 39. At the same time power click 41 is pushing elastic stops 45, and guide pin 5 at the speed V toward cooling vessel 6 (FIG. 20). At this time pullback spring 42 gets compressed. As all electric processes are happening fast (about millisecond) so mechanical processes is progressing extremely fast, taking form of impulse push.

Figure 16:
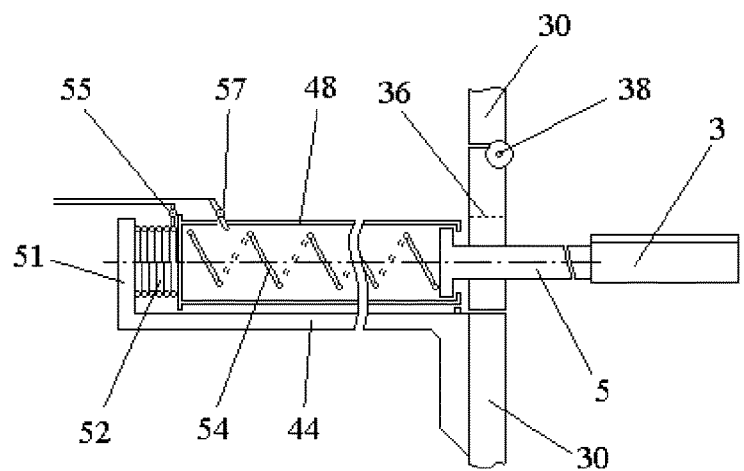
FIG. 16—is a schematic view of a starter device on FIG. 15 with first section activation (transition)

If motor drive 1 is performed as two-sectioned coaxial starter device of telescopic type (FIG. 15), then to start, controlled clamp 57 is to be pressed. At this time compressed spring 54 is being released by indicated clamp and it's pushing guide pin 5 with container 3 forward (FIG. 16).

Figures 8, 9, 10:
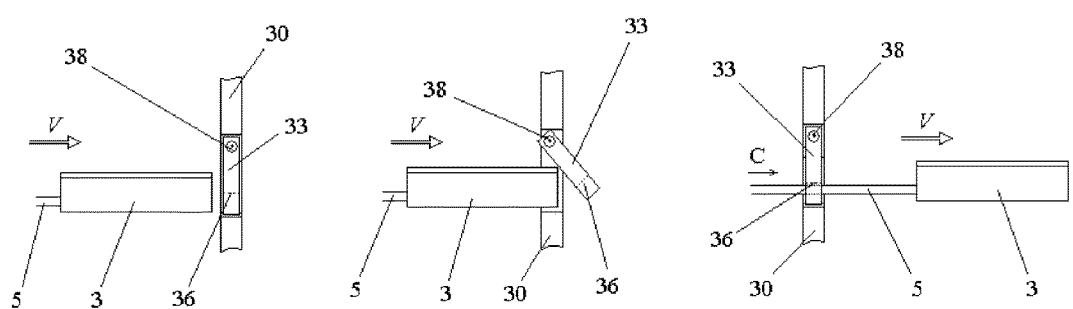
FIG. 8—is an insulating curtain position before container's penetration.
FIG. 9—is an insulating curtain position at the moment of container penetration.
FIG. 10—is an insulating curtain position after container penetration.

After starting linear percussion stepping motor drive 1, container 3 quickly transfers from environment temperature zone 2 to cooling vessel 6 (FIG. 2). While going through vertical wall 30 of vessel 6, container 3 is pushing heat insulating curtain 33, which turns around horizontal axis 38, lifting bottom end (FIG. 9). After container 3 passed the wall 30 heat insulating curtain 33 is turning its axis 38 invertedly, putting down the bottom end, taking original position (FIG. 10). And guide pin 5 is settling in curtain 33 split 36 (FIG. 11).

After discharging process is finished currents in inductor 39 and electro conductive anchoring block 40 decay and electrodynamic force between them goes to zero. Compressed pullback spring 42, when being released returning power disc 41 and anchoring block 40 to original positions at the speed v, toward inductor 39 (FIG. 21). At this motion, power disc 41, while going through elastic stops 45, turning them around axis 47, compressing spring 46 (FIG. 22). After power disc passed, spring 46 is released, returning stops 45 to original positions (FIG. 20).

Figure 5:
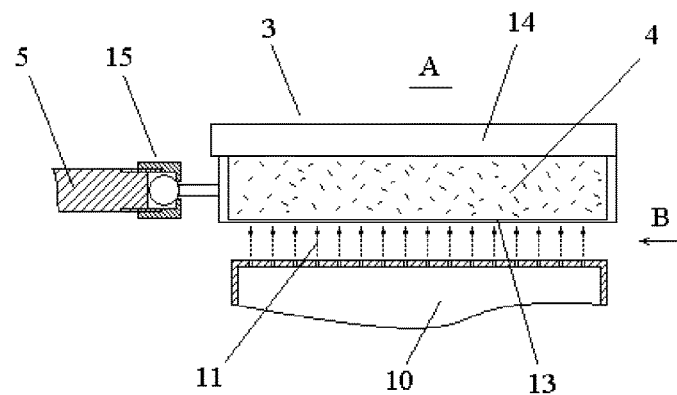
FIG. 5—is part A on FIG. 2.
Figure 6:
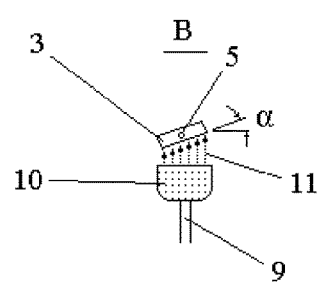
FIG. 6—is part B on FIG. 5.

In vessel 6 container is going under liquid nitrogen inclined upflow 11, which is affecting bottom panel 13 of flat ended container 3 (FIG. 5, 6). Jets 11 of liquid nitrogen are intensively pushing vapor film formed on the bottom panel 13 of container 3 through and removing it. Since bottom panel 13 of container is thin, made from heat conductive material such as copper for example, so thin biological specimen 4 is being cooled intensively, simultaneously in its entire area. Removal (expulsion) of evaporated nitrogen from bottom panel 13 of flat ended container 3 is encouraged by inclined liquid nitrogen flow. Besides, since container is inclined, condition of the biological specimen 4 can be easily watched from environment temperature zone 2 through container cover lid 14 and vacuum window 16 of vessel 6, which are made from thermal glass.

Evidence of container 3 complete refrigeration is absence of vapor film on flat ended container 3 bottom panel 13, when it's fully immersed in liquid nitrogen 21.

Figure 3:
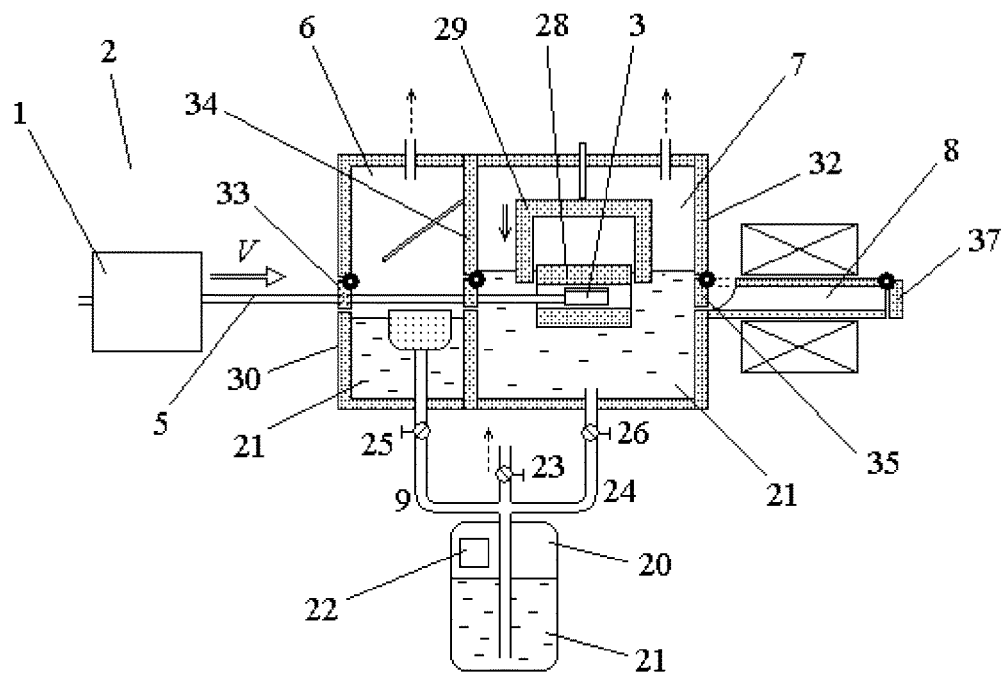
FIG. 3—is a device on FIG. 1 at the moment when container is placed in storage vessel.

After vessel 6 is filled with liquid nitrogen, shutoff valve 25 is to be closed and supply of liquid nitrogen to filled cooling vessel 6 stops. (FIG. 2, FIG. 3). Shutoff valve 26 is getting opened and liquid nitrogen 21 from containment vessel 20 goes through heat insulated nozzle 24 to storage vessel 7, filling it. With that evaporated gaseous nitrogen is going out through nozzle 18 from vessel 7 to environment temperature zone 2, ensuring preservation of atmospheric pressure in this vessel. Shutoff valve 26 is to be closed.

After this, under power pulse action, created by linear percussion stepping motor drive 1, container 3 transfers to filled with liquid nitrogen 21 storage container 7 from neighboring cooling vessel 6 (FIG. 3). With that container 3 ends up in fixed part 28 of holding system 27.

Figure 17:
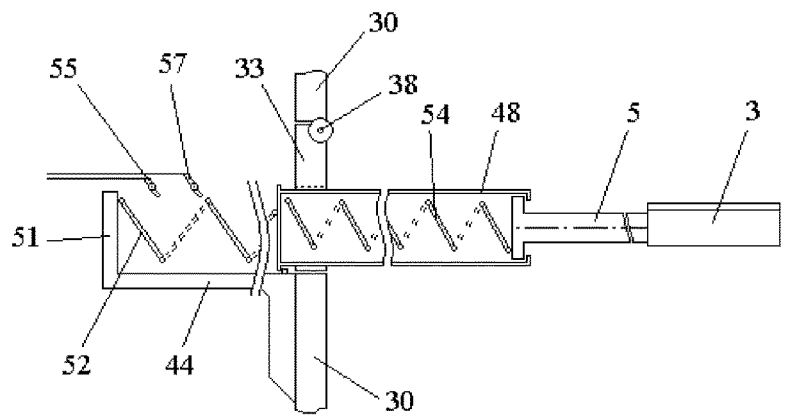
FIG. 17—is a schematic view of a starter device on FIG. 15 with first and second section activation (transition)
Figure 18:
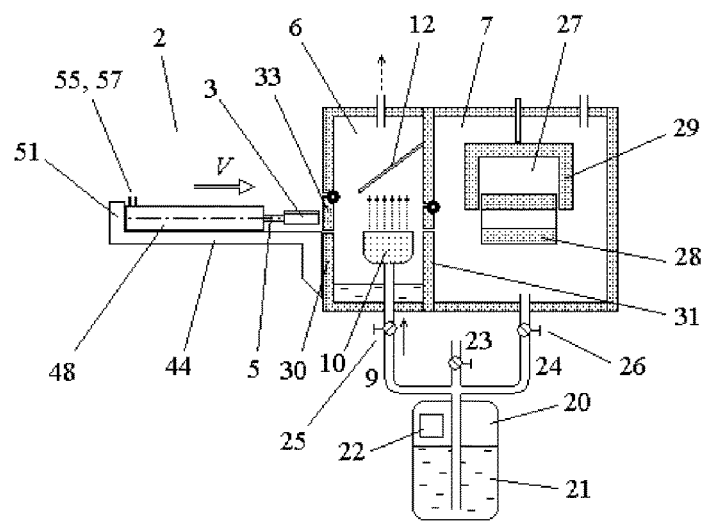
FIG. 18—is a schematic view of specimen hyper-fast cooling and storage device and coaxial starter device of telescopic type.

If motor drive 1 is performed as two sectioned coaxial starter device of telescopic device (FIG. 15), then controlled clamp 55 is pressed. So compressed spring 52 is being released by indicated clamp, pushing guide pin 5 with container 3 forward (FIG. 17).

Figure 7:
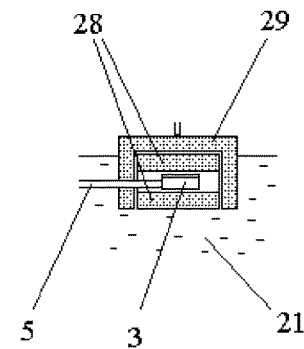
FIG. 7—is a fixation of the container in storage vessel.

For container 3 prolonged storing in vessel 7, where there's room for various manipulation with vessel 7, such as transportation, transfer to different conditions and others, fixed part 28 of holding system 27 is to be closed by moving element 29 (FIG. 7). At this time container can be disconnected from guide pin 5 by ball clamp 15. Like this, holding system 27 together with container 3 is safely secured in vessel 7, from different mechanical vibration for example and it can be transferred inside vessel 7, providing room for following containers. All heating and mechanical processes can be watched from zone 2 through window 16, located on this vessel side wall (FIG. 12).

If necessary to hyper-fast heat biological specimen 4, following actions are to be performed.

Electric heater 22 is to be turned off, shut off valves 25 and 26 are to be closed, and pressure release valve 23 is to be opened. So gaseous nitrogen of increased pressure is going out from containment vessel 20 through valve 23 to environment temperature zone 2. After gas pressure equalizing in zone 2 and in vessel 20 shutoff valves 25 and 26 are to be opened and liquid nitrogen from cooling vessel 6 and storage vessel 7 is to be drained to containment vessel. 20 (FIG. 4).

Figure 4:
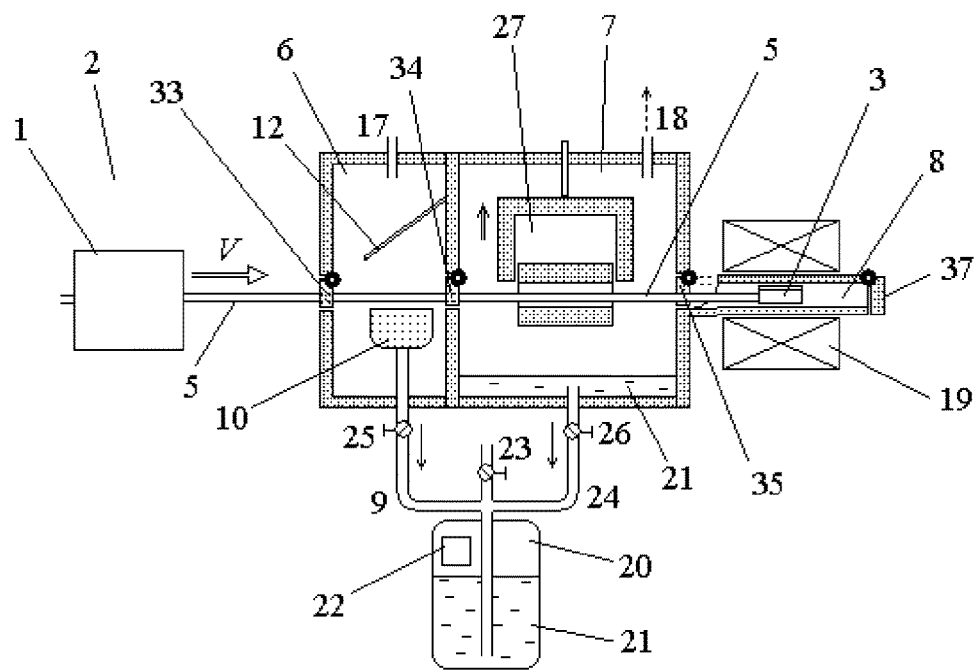
FIG. 4—is a device on FIG. 1 at the moment when container is placed in heating vessel.

After this, under power pulse action, created by linear percussion stepping motor drive 1, container 3 transfers from neighboring storage vessel 7 to active zone of heating device 8, where HP magnetic field is created before by source 19 (FIG. 4).

While container 3 is going through walls 31 and 32, between vessels 6 and 7, 7 and 8 heat insulating curtains 34 and 35 are acting similar to curtain 33 when going through wall 30.

Hyperast heating of biological specimen 4 located in container 3 is possible because of:
active zone of heating device 8, is located in environment temperature zone 2, which significantly exceeding liquid nitrogen temperature in vessel 7;
HP magnetic field, created by the source 19, is heating biological specimen 4 directly;
HP magnetic field, created by the source 19, is heating bottom panel 13 of container 3, which made from copper, and the panel is heating specimen 4 by thermal conductivity.

After biological specimen 4 achieved environment temperature, HP magnetic field source 19 is to be turned off and container 3 is to be transferred by linear percussion stepping motor drive 1, from active zone of heating device 8 to zone 2 (not shown on the drawing).

In storage device and hyper-fast heating device of specimen (FIG. 19), located at the end of guide pin 5, clamp 58 is positioning container 3 in storage vessel 7, performing its further transferring to vessel 8.

In presented device low flow of liquid nitrogen is assured by its multiple transfer from containment vessel to cooling vessel and storage vessel and back, which makes the process cost efficient.

The process of cooling and manipulation in cooling and storage vessel is producible and controlled visually through vacuum windows 16 on every basic stage, which allows to modify conditions of the process such as jets speed in cooling vessel and others.

Device of hyper-fast cooling and heating of specimen, using motor drive with linear and rotary motion (FIG. 23-FIG. 36) works as follows:

In initial condition valves 23, 25 and 71 are to be closed, and heater 22 is to be turned on. Thereby increased pressure of gaseous nitrogen creates in containment vessel 20.

Figure 23:
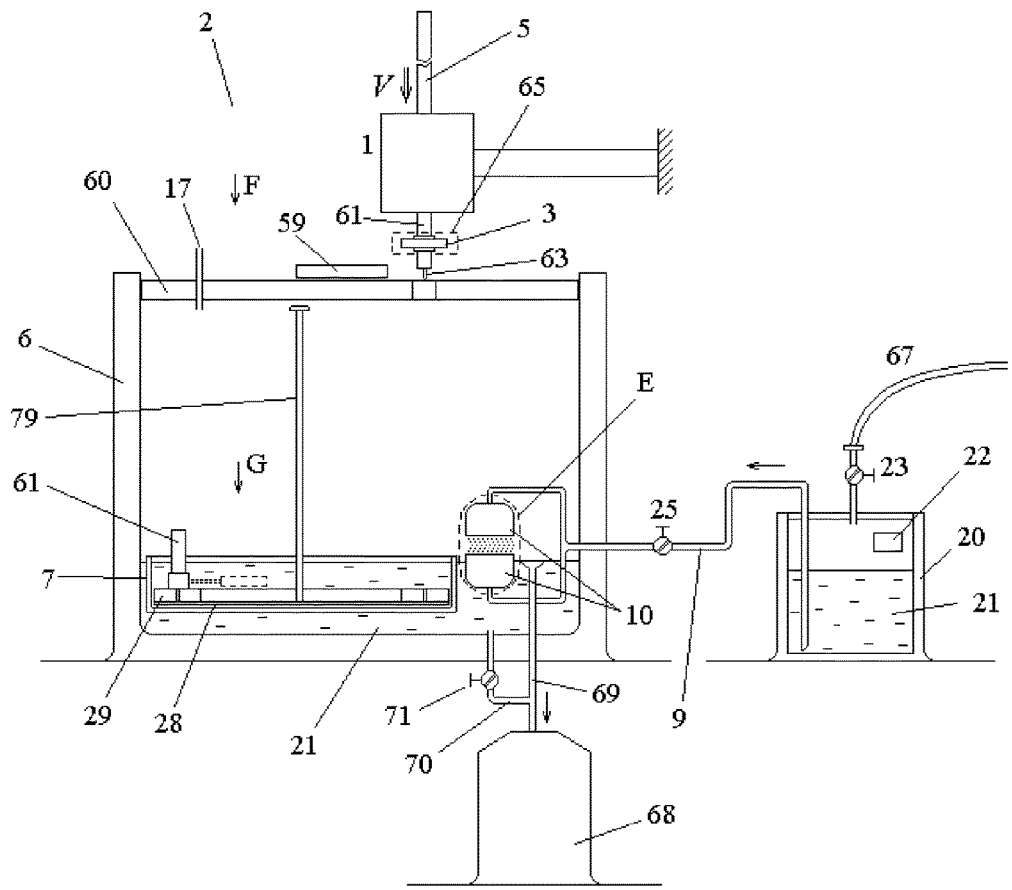
FIG. 23—is a schematic view of specimen hyper-fast cooling and heating device using cryogenic refrigerant and a motor drive, which provides linear and rotation motion, before placing container in cooling vessel (without side walls).

Guide pin 5 with sectional end unit 61 raises, and to it container 3 biological specimen is secured with bar 64 and heat-insulated capsule 65 is secured with bar 66 (FIG. 23). End unit 61 of pin releases elastic clamps 62. Container 3 is to be placed inside heat insulating capsule 65 in environment temperature zone 2

After valve 25 gets opened and increased pressure liquid nitrogen 21 comes in cooling vessel 6 from containment vessel 20 via atomizers 10 of nozzle 9. Evaporated gaseous nitrogen is going out through nozzle 17 from vessel 6. If level of liquid nitrogen 21 in vessel 6 exceeds top piece of nozzle 69, it discharges in cryogenic vessel 68.

After, moving heat insulating curtain 59 is being displaced sideways, split at cover lid 60 of cooling vessel 6 is being opened, and motor drive 1 with guid pin 5 provides linear transferring at the speed V container 3 together with heat insulating capsule 65 inside vessel 6.

After sectional end part 61 of pin 5 contacts with container holding system 27, container is turned with speed ω, for example 90° (FIG. 35), the way that container 3 enters non-contact/contactless in gap between atomizers 10 (FIG. 30). Since distance between atomizers 10 is less than matching dimensions of heat insulation capsule 65, it is set against atomizers and moved from container 3 (FIG. 24). With that container 3 is cooling intensivly by jets 11 of liquid refrigerant 21, at the angle α, which helps removal of nitrogen vapor film on flat container panels, and therefore elimination of the Leidenfrost effect.

After contact of sectional/detachable end piece 61 of pin 5 with a moving part 29 of holding system 27, central pivot 63 ends up/is going in holding/fixing split 74 of section 73 of moving part 29. Stop 77, under effect central pivot 63 of guid pin 5, is pressed down and releases matching stop 76 of section 73 (FIG. 28, FIG. 30). With that, end unit 61 of pin 5 is fixed with section 73 of moving unit 29 of holding system 27.

Moving insulating curtain 59 returns to original position, and split closes at cover lid 60 of cooling vessel 6.

Figure 25:
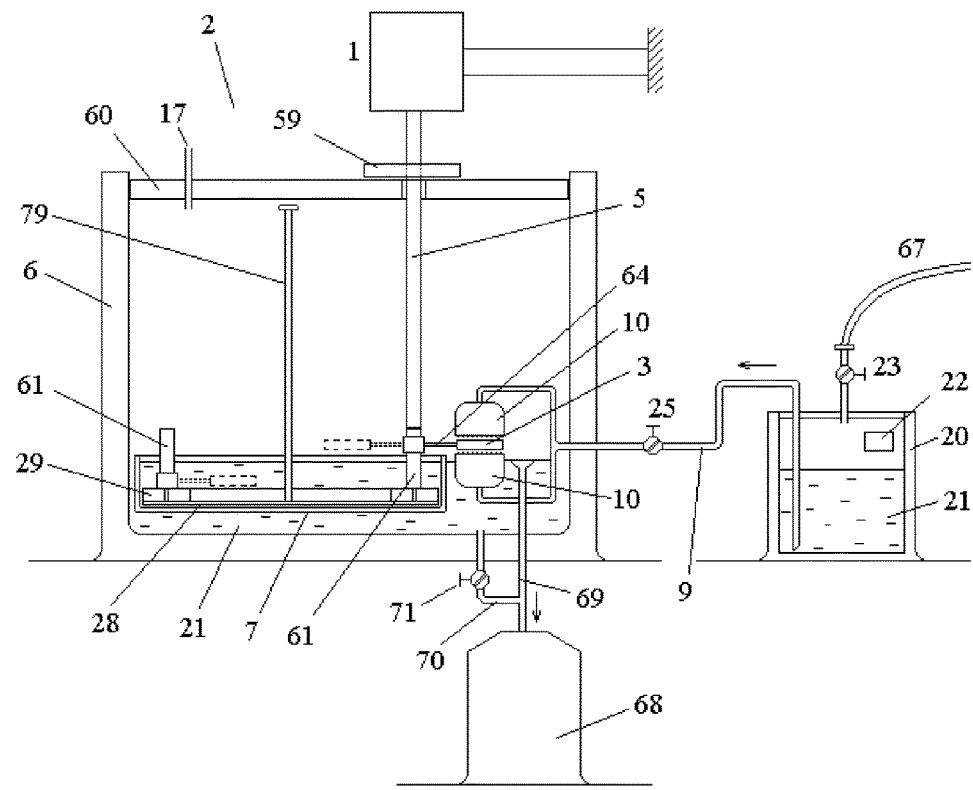
FIG. 25—is a device on FIG. 23 after placing container in cooling vessel.
Figure 31:
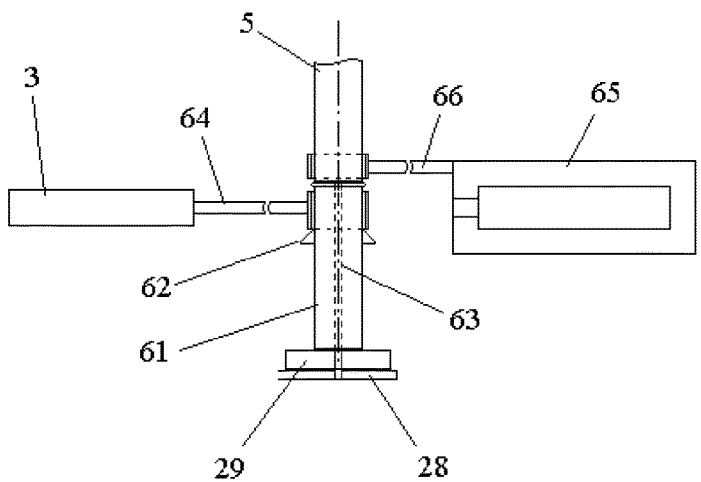
FIG. 31—is a device on FIG. 30 after container moved out of zone of cryogenic refrigerant jets atomizers.

After cooling container 3 to the temperature of liquid nitrogen, guide pin 5 further is turned, and container 3 with bar 64 (bar on FIG. 24, and container on FIG. 25 are shown by dashed lines) is installed opposite storage vessel 7 (FIG. 31).

Figure 32:
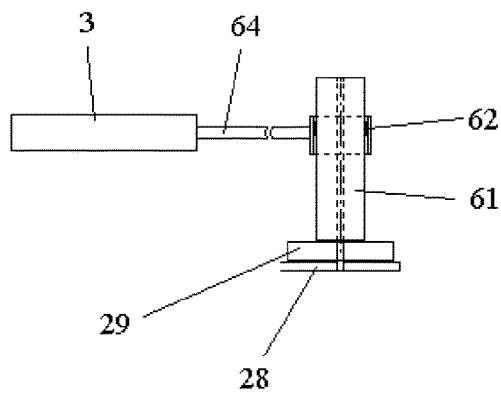
FIG. 32—is a device on FIG. 31 at the first moment after a guide pin raised.
Figure 33:
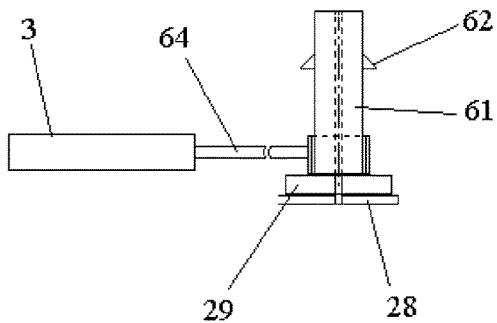
FIG. 33—is a device on FIG. 32 after container pull down.
Figure 34:
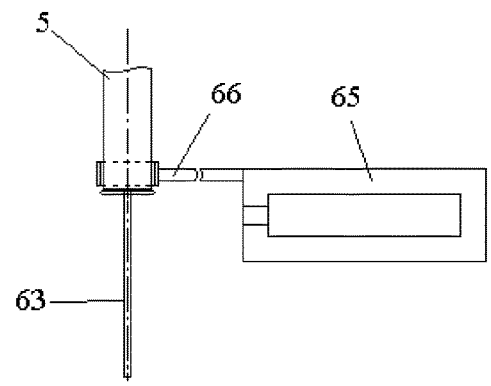
FIG. 34—guide pin without sectional end part of the pin with heat-insulated capsule.
Figure 35:
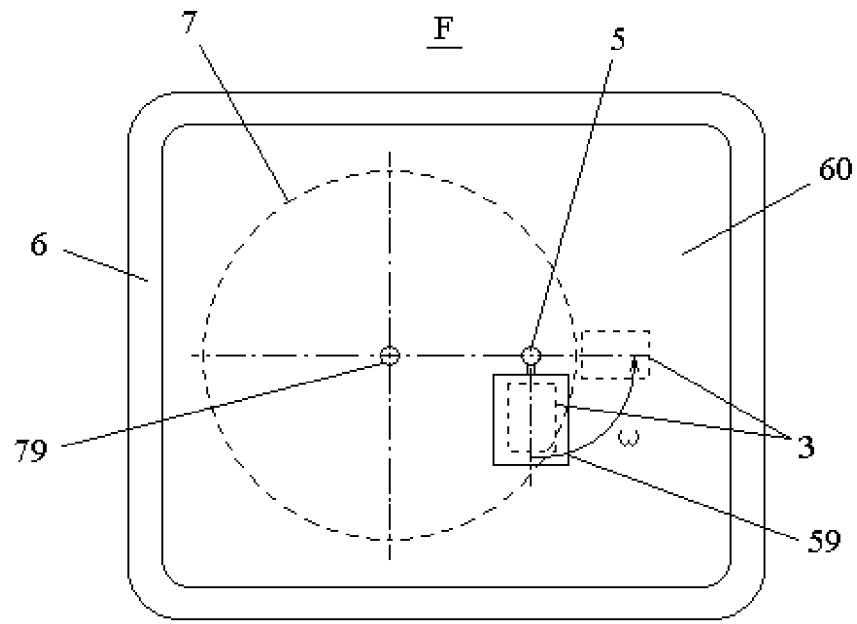
FIG. 35—is a view F on FIG. 23.
Figure 36:
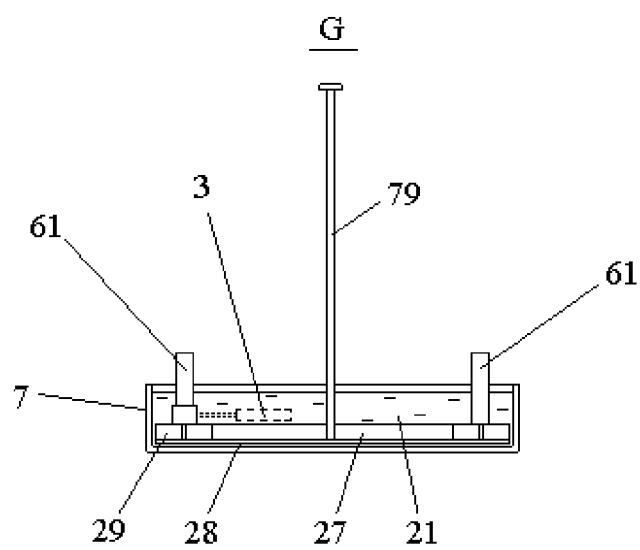
FIG. 36—vessel storage container.

Guide pin 5 detaches from end unit/piece 61 and raises with heat insulating capsule 65. Elastic clamps 62 are being compressed, providing sinking bar 64 with container 3 down to storage vessel 7 (FIG. 32, FIG. 33). With spring 75 section 73 is discrete transferring together with end unit/piece 61 and container 3 (FIG. 27) till stop 76 of next section 73 contacts stop 77 which is located on fixed piece/unit 28 of holding system 27. Thus, a series of containers 3 can be fixed in storage vessel 7 (on FIG. 27 shown by dashed lines).

After the end of containers 3 cooling process, valve 71 is to be opened and liquid nitrogen 21 through nozzle 70 is discharged from cooling vessel 6 to cryogenic vessel 68.

Cover lid 60 is to be opened and with handle 79 storage vessel 7 with containers 3 is taking out from vessel 6 and is transferring in necessary place, in cryogenic transport vessel for example (not shown on the drawing).

If necessary, fast heating storage container 7 with handle 79 is transferring inside heating vessel 72. Motor drive 1 is putting down guid pin 5 into vessel 72 till it is contacting and joining with end part 61. After with guid pin 5 and bar 64, container 3 is raising and turning, beyween two elements 78 of heating device 19, untill entering into the gap (FIG. 26). With HP magnetic field source or hot compressed gas container 3 is cooling rapidly to the desired temperature.

A container 3 (FIGS. 37-39) that has inlet 82 and outlet 83 valves and highly thermo conductive spiral inside allows to make the container to be technologically convenient and substantially increase the rate and homogeneity cooling and spatial homogeneity of temperature distribution inside, which especially important for scale-up large volume containers.

Ultra-high rates of cooling of biological specimens are achieved by:
- contact of numerous liquid nitrogen jets, with significant motional energy, on all wide, flat area of cooled biological specimen through thin copper wall of container;
- short life of vapor phase (film boiling) on the contact border of liquid nitrogen with biological specimen;
- "force" removal of vapor phase by directed flow of liquid nitrogen (under pressure);
- percussive-dropping cooling by multiple contacts of liquid nitrogen with biological specimen surface.

The invention claimed is:

1. A system for hyper-fast cooling of biological samples, comprising:
   a cooling chamber comprising an atomizing nozzle for directing a flow of liquid cryogenic refrigerant against a surface of a container of the biological samples for cooling the biological samples at a rate of 50,000° C/minute or greater, and further comprising a first heat insulating curtain located at a first position on a first vertical wall of the apparatus for allowing the container to pass through the first vertical wall;
   a storage chamber coupled to the cooling chamber by a common vertical wall, the storage chamber comprising:
      a holding system for storing the container after it has been hyper-cooled by the flow of liquid cryogenic refrigerant from the atomizing nozzle; and
      a second heat insulating curtain located at a second position on the common vertical wall in horizontal alignment with the first heat insulating curtain; and
      a percussion motor drive coupled to the container for propelling the container horizontally into the cooling chamber through the first heat insulating curtain, placing the container adjacent to the atomizing nozzle, and which further acts to propel the container through the common wall and into the storage chamber, via the second heat insulating curtain, after the biological samples have been hyper-cooled;
   and;
   a warming chamber, comprising;
      a second common wall located opposite to the common wall;
      a third heat insulating curtain located at a third position on the second common wall, the third heat insulating curtain in horizontal alignment with the first and second heat insulating curtains; and
      a heating device located adjacent to the third heat insulating curtain for heating the biological samples, the heating device comprises a magnetic field source;
   wherein the percussion motor drive is further configured to extend the container horizontally through the storage chamber and into the warming chamber.

2. The system of claim 1, wherein the first and second heat insulating curtains comprise a split for allowing the container to pass, and installed with an ability to rotate around a horizontal axis located above each of the curtains.

3. The system of claim 1, wherein guide pin is connected to the container by a ball clamp.

4. The system of claim 1, wherein the container comprises a flat-ended box comprising a bottom panel made of a heat conductive material, and a top cover that is made from an optically transparent material.

5. The system of claim 1, wherein the holding system comprises a fixed portion and a moving portion that captures the container.

6. The system of claim 1, wherein the cooling chamber further comprises a deflector for deflecting the flow of liquid cryogenic refrigerant flow.

7. The system of claim 1, wherein the atomizer nozzle is installed at an angle with respect to a bottom surface of the container.

* * * * *